United States Patent [19]

Buckland et al.

[11] Patent Number: 4,777,121

[45] Date of Patent: Oct. 11, 1988

[54] SUBSTITUTED PYRAZOLO[3, 2-C]-S-TRIAZOLE PHOTOGRAPHIC COUPLERS AND PHOTOGRAPHIC MATERIALS AND PROCESSES EMPLOYING THEM

[75] Inventors: Paul R. Buckland, St. Albans; Llewellyn J. Leyshon, Watford, both of United Kingdom

[73] Assignee: Eastman Kodak Company, Rochester, N.Y.

[21] Appl. No.: 128,377

[22] Filed: Dec. 3, 1987

Related U.S. Application Data

[63] Continuation of Ser. No. 845,304, Mar. 28, 1986, abandoned.

[30] Foreign Application Priority Data

Apr. 3, 1985 [GB] United Kingdom ............... 8508756

[51] Int. Cl.$^4$ ................ G03C 7/36; G03C 7/38
[52] U.S. Cl. ................ 430/386; 430/387; 430/558
[58] Field of Search ............ 430/558, 386, 387, 551, 430/372

[56] References Cited

U.S. PATENT DOCUMENTS

| | | | |
|---|---|---|---|
| 3,647,452 | 3/1972 | Hendress et al. | 96/55 |
| 3,705,896 | 12/1972 | Bailey et al. | 430/558 |
| 3,725,067 | 4/1973 | Bailey et al. | 430/558 |
| 4,254,216 | 3/1981 | Uchida et al. | 430/551 |
| 4,548,899 | 10/1985 | Nakayawa et al. | 430/558 |
| 4,562,146 | 12/1985 | Masuda et al. | 430/546 |
| 4,588,679 | 5/1986 | Furutachi | 430/551 |
| 4,600,688 | 7/1986 | Kawakatsu et al. | 430/558 |
| 4,607,002 | 8/1986 | Nakayawa et al. | 430/505 |

FOREIGN PATENT DOCUMENTS

| | | |
|---|---|---|
| 82732 | 6/1983 | European Pat. Off. . |
| 1247493 | 9/1971 | United Kingdom . |
| 1252418 | 11/1971 | United Kingdom . |
| 1398979 | 6/1975 | United Kingdom . |
| 2004087 | 9/1978 | United Kingdom . |

OTHER PUBLICATIONS

Research Disclosure, Aug. 1974, Item No. 12443.
Research Disclosure, Dec. 1978, Item No. 17643.

Primary Examiner—Paul R. Michl
Assistant Examiner—Lee C. Wright
Attorney, Agent, or Firm—Richard E. Knapp

[57] ABSTRACT

Pyrazolo[3,2-c]-s-triazole dye-forming couplers containing in the 6-position a substituted or unsubstituted tertiary alkyl group and in the 3-position a substituted or unsubstituted aryl group in photographic materials and processes provide dyes of improved light stability. These couplers are particularly useful in combination with alkoxybenzene dye image stabilizers.

14 Claims, No Drawings

SUBSTITUTED PYRAZOLO[3, 2-C]-S-TRIAZOLE PHOTOGRAPHIC COUPLERS AND PHOTOGRAPHIC MATERIALS AND PROCESSES EMPLOYING THEM

This is a continuation of application Ser. No. 845,304, filed 3/28/86, now abandoned.

This invention relates to novel pyrazolo-[3,2-c]-s-triazole compounds useful as magenta dye-forming couplers in color photographic processes, to a method of making these compounds, and to image dyes formed therefrom.

In a common form of color photographic process, developable silver halide grains in a photographic emulsion layer are developed with a color developer solution containing a p-phenylenediamine color developing agent, and the oxidized developing agent so produced reacts with a coupler to produce an image dye. The coupler is usually incorporated in the emulsion, or an adjacent layer, but may be a constituent of the developer solution. Any undeveloped grains and the silver produced from the developed grains are subsequently removed, commonly with a bleach-fix bath. Pyrazolone couplers are frequently employed for giving magenta image dyes, but other classes of compound have been suggested including pyrazolo[3,2-c]-s-triazoles, as described in, for example U.K. Patent Specification Nos. 1,247,493; 1,252,418; and 1,398,979.

Pyrazolo[3,2-c]-s-triazole compounds of the general type proposed for use as color couplers may be represented by the general formula:

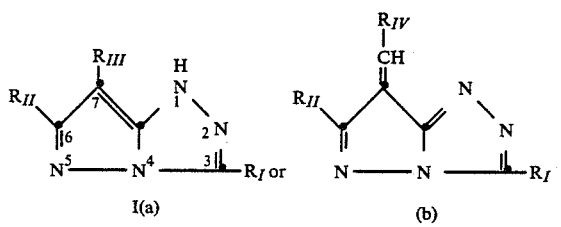

I(a)     (b)

wherein $R_I$ and $R_{II}$ are substituents chosen to give the coupler the desired solubility and diffusion resistance, and also to give the image dye obtained by color development using the coupler, the desired color, and $R_{III}$ and $=CHR_{IV}$ are moieties which leave the coupling (7-)position when, during color development, the coupler reacts with oxidized color developing agent. Pyrazolotriazole couplers are commonly made by the method of Bailey (J. C. S. Perkin 1, 2047 (1977)) in which the compound:

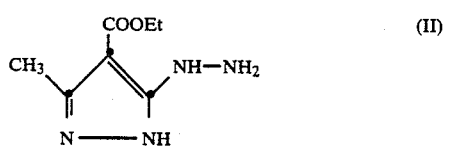

is condensed with an aldehyde to give a hydrazone which is converted, by oxidative cyclization, to the desired pyrazolotriazole. This method gives a product in which $R_{II}$ of Formulae (I)a and (b) is methyl. Another method which has been suggested for making these couplers is described in Research Disclosure, Item 12443, August 1974. This method is based on a thermal extrusion of sulfur from a s-triazolo[3,4-b]-[1,3,4] thiadiazine with concomitant ring contraction and allows a variety of substituents $R_{11}$ to be obtained at the 6-position. Example 5 of this disclosure describes the preparation of 7-tert-butyl-3-methyl-1H-pyrazolo[3,2-c]-s-triazole; the yield was only 21%.

Although numerous pyrazolotriazole couplers are known in the photographic art, a continuing search has gone on for new pyrazolotriazole couplers which improve upon existing pyrazolotriazole couplers or can be prepared by advantageous new methods. Such a coupler is particularly desirable if it provides a more stable image dye upon oxidative coupling.

This invention provides a new class of pyrazolo[3,2-c]-s-triazole dye-forming couplers containing in the 6-position a substituted or unsubstituted tertiary alkyl group and in the 3-position a substituted or unsubstituted aryl group. Such couplers provide magenta image dyes upon oxidative coupling in photographic elements that have improved light stability compared to magenta image dyes provided by, for example, the same couplers but with a methyl group in the 6-position rather than a tertiary alkyl group.

Particularly useful couplers are pyrazolotriazoles of the formulae:

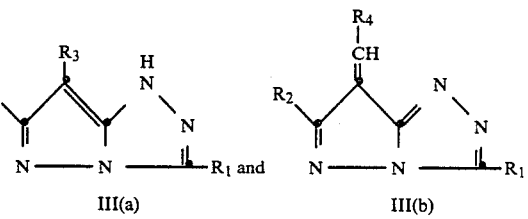

III(a)     III(b)

wherein $R_1$ is an aryl or substituted aryl group, $R_2$ is a tertiary alkyl group, which may be substituted or unsubstituted, and $R_3$ and $=CH-R_4$ are moieties which are displaced when the compound reacts with an oxidized color developing agent, particularly a p-phenylenediamine color developing agent.

The image dyes from the couplers of Formulae III(a) and (b) may be further stabilized to light using members of a class of compounds selected from the class of substituted benzene image stabilizers described in U.K. Patent Application No. 2,004,078A.

The pyrazolotriazole couplers of the Formulae III(a) and (b), the image dyes obtained from them by color development, are new compounds. A new method of synthesizing these couplers has been devised, and the 7-cyanopyrazolotriazole compounds used therein are new.

In the Formulae III(a) and (b), $R_1$ is preferably phenyl or naphthyl. The phenyl and naphthyl are unsubstituted or are preferably substituted with groups which advantageously influence the properties of the coupler and the image dye formed from the coupler. Examples of useful substituents are alkyl, such as alkyl containing 1 to 20 carbon atoms, for example methyl, ethyl, propyl, butyl, pentyl, decyl and eicosyl; halogen, such as chloro, bromo and fluoro; and ballast groups which are known to be useful on photographic couplers. Particularly useful $R_1$ groups are phenyl groups containing alkyl groups, such as methyl or ethyl groups, in at least two of the 2-, 4- and 6-positions of the phenyl groups. As described hereinafter, $R_1$ may comprise a ballast moiety, or a second pyrazolotriazole nucleus, in which case it may complete a symmetrical bis-pyrazolotriazole. Examples of useful $R_1$ groups are:

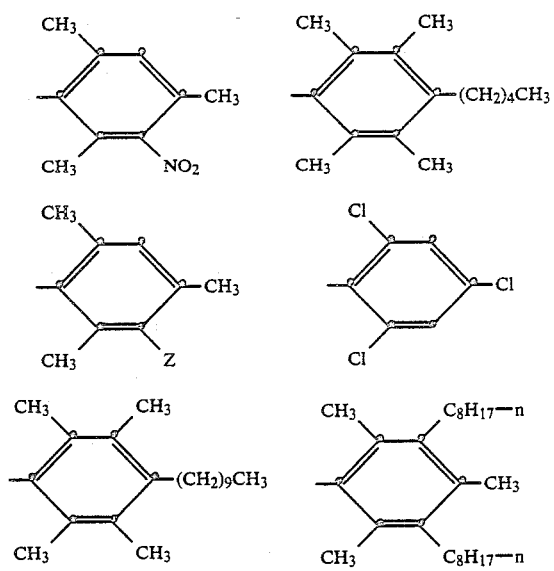

wherein Z is a ballast group known in the photographic art.

The tertiary alkyl group $R_2$ preferably contains from 4 to 20 carbon atoms and is unsubstituted or contains such simple substituents as halogen atoms, such as chlorine, bromine or fluorine, alkoxy groups, such as methoxy and ethoxy, or nitro groups. Examples of useful tertiary alkyl groups are t-butyl, t-pentyl, and t-octyl groups.

$R_3$ is preferably hydrogen, halogen, carboxyl, alkylthio, arylthio, or aryloxy, but any coupling-off group, as described as a leaving group, can be used. The coupling-off group can be introduced in the 7-position of the coupler in a known manner as described in, for instance, U.K. Patent Specification No. 1,334,515. Other examples of leaving groups are sulfonic acid, acyloxy, amino, arylthio, aryl- or heterocyclic-azo (possibly providing colored couplers) and releasable photographically useful groups (PUGs) known in the photographic art, such as developing inhibitor releasing (DIR) groups and heterocyclic, such as benzotriazolyl groups.

$R_4$ is preferably an aryl or heterocyclic group, optionally containing such substituents as halogen atoms, alkyl, alkoxy, hydroxyl and nitro groups and sulfonic acid carboxylic acid and ester groups. $R_4$ may also be atoms completing a methine dye. Preferred heterocyclic groups for $R_3$, or for inclusion in $R_1$, $R_3$ or $R_4$ comprise 5- or 6-membered heterocyclic rings containing one or more atoms selected from oxygen, sulfur, selenium and nitrogen atoms, these rings optionally being fused with one or more carbocyclic or heterocyclic rings of 5 or 6 members.

The new synthetic method of the invention uses, as a starting material, a 2-acyl-3,3-bis(methylthio)acrylonitrile (IV) of the formula $R_2COC(CN)=C(SCH_3)_2$ wherein $R_2$ is the tertiary alkyl group required for the 6-position of the coupler being made. This starting material can be obtained by reacting carbon disulfide with a compound of formula $R_2COCH_2CN$ to give a compound of formula $R_2COC(CN)=C(SH)_2$ and then treating this with methyl iodide.

The substituted acrylonitrile (IV) is reacted with t-butylcarbazate (V) to give an intermediate (VI) of the formula:

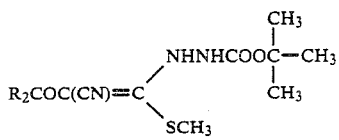

which is reacted with hydrazine hydrate to produce a substituted pyrazole (VII) of the formula:

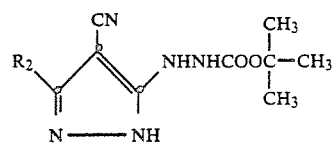

This can be treated with a concentrated acid such as hydrochloric acid to give a 3(5)-hydrazinopyrazole (VIII) from which a pyrazolo[3,2-c]-s-triazole can be prepared by known procedures. A diagram of the described reaction steps is as follows:

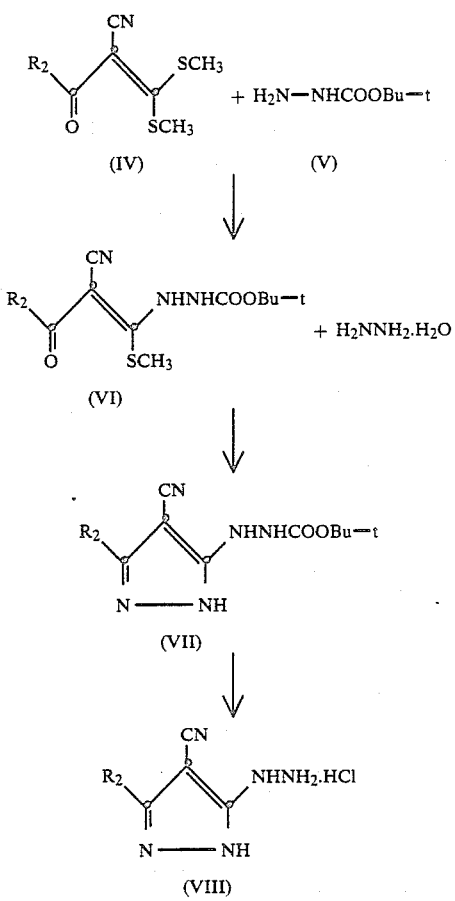

Procedures appropriate for obtaining a 3-arylpyrazolo[3,2-c]-s-triazole from the intermediate (VIII) include reaction with an aromatic aldehyde (ArCHO) (IX) or acid chloride (ArCOCl) (X) followed by ring closure, which can be effected using bromine and sodium acetate in acetic acid or phosphorus oxychloride in an inert solvent. The reactions are as follows:

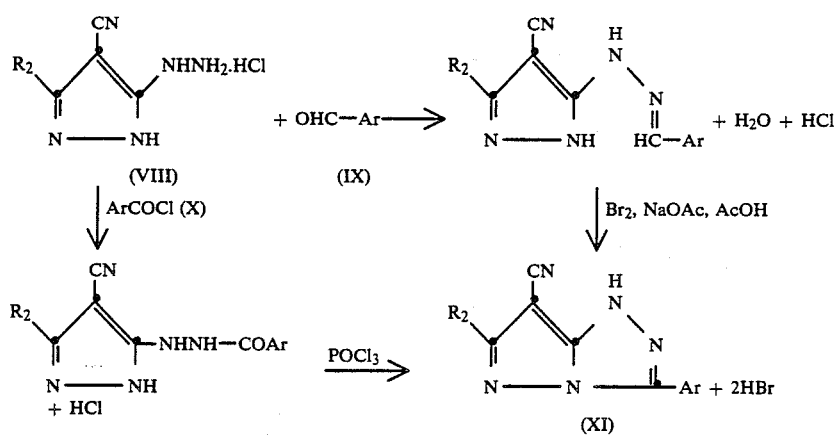

The cyano group can be removed from the 7-position by hydrolysis and decarboxylation in situ of the resulting carboxylic acid, for example, by heating the compound (XI) in 80% sulfuric acid. If a leaving group is desired at that position, it can be introduced in known manner, the 1-nitrogen atom being blocked if necessary, by acetylation for instance, during the process. Again, it may be necessary to block the 1-nitrogen atom if it is desired to introduce any additional substituent, or substituents, into the 3-aryl substituent so as to alter the solubility of diffusibility of the coupler molecule.

As is well known, ballast groups can readily be attached by providing an amino group in the coupler at the desired point of attachment and reacting this with a carbonylhalide-substituted ballast molecule. In this way ballast groups such as those of the general formulae:

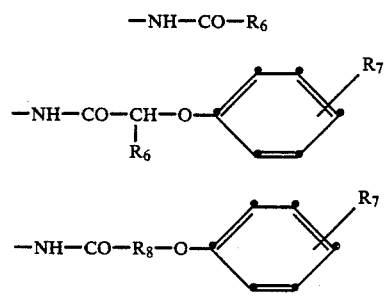

can be provided, each $R_6$ representing an alkyl group, each $R_7$ representing one or more substituents, such as alkyl, aryl and substituted aryl substituents, and $R_8$ representing an alkylene group. The numbers of carbon atoms in the various R groups are chosen to give the desired solubility and bulk. Ballast groups of other types can be used, including those of the following formulae wherein $R_7$ and $R_8$ are as defined above.

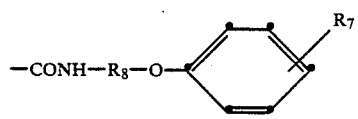

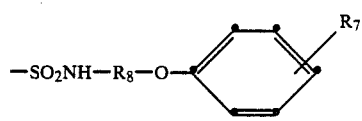

Procedures for introducing all these, and other, kinds of ballast groups are described in the organic compound synthesis art and the photographic art, some references to patents concerned with color couplers being given in *Research Disclosure*, Section VII. In the couplers of the invention either or both of $R_1$ and $R_2$ may contain one or more ballast groups.

Specific examples of the new pyrazolo[3,2-c]-s-triazole couplers are the following compounds, which are numbered for convenience of reference in the examples hereinafter.

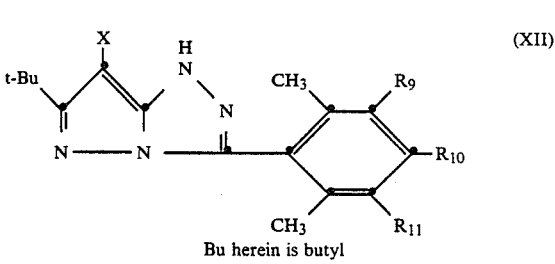

Bu herein is butyl

TABLE 1

| Coupler No. | X | $R_9$ | $R_{10}$ | $R_{11}$ |
|---|---|---|---|---|
| 1 | H | H | CH$_3$ | —NO$_2$ |
| 2 | H | H | CH$_3$ | Ballast A |
| 3 | Cl | H | CH$_3$ | Ballast A |
| 4 | H | CH$_3$ | (CH$_2$)$_9$CH$_3$ | CH$_3$ |
| 5 | H | H | CH$_3$ | Ballast B |
| 6 | Cl | H | CH$_3$ | Ballast C |

TABLE 1-continued

| Coupler No. | X | $R_9$ | $R_{10}$ | $R_{11}$ |
|---|---|---|---|---|
| 7 | H | $C_8H_{17}(n)$ | $CH_3$ | $C_8H_{17}(n)$ |

Ballast A

—NHCOCHO(—$C_{12}H_{25}(n)$)—⟨phenyl⟩—NH.SO₂Bu(n)

Ballast B

—NHCOCHO(—$C_{12}H_{25}(n)$)—⟨phenyl⟩—SO₂—⟨phenyl⟩—OH

Ballast C

—NHCO(CH₂)₃O—⟨phenyl with $C_5H_{11}(t)$ substituents⟩—$C_5H_{11}(t)$

The couplers of this invention can be used in ways and for purposes that couplers are used in the photographic art.

Preferably the couplers are incorporated in silver halide emulsions and the emulsion coated on a support by methods known in the photographic art to form a photographic element. The couplers optionally can be incorporated in photographic elements adjacent the silver halide emulsion where, during development the coupler will be in reactive association with oxidized color developing agent. Thus, herein the term "associated therewith" means that the coupler is in at least one silver halide emulsion layer or in an adjacent location where, during processing, the coupler will come into reactive association with oxidized color developing agent.

A photographic element according to the invention can be a single color element or preferably a multicolor element. Multicolor elements can contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art. In an alternative format, the emulsions sensitive to each of the three primary regions of the spectrum can be disposed as a single segmented layer.

A typical multicolor photographic element comprises a support bearing a cyan dye image-forming unit comprised of at least one red-sensitive silver halide emulsion layer having associated therewith at least one cyan dye-forming coupler, a magenta dye image-forming unit comprising at least one green-sensitive silver halide emulsion layer having associated therewith at least one magenta dye forming coupler according to the invention and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like.

In the following discussion of suitable materials for use in the emulsions and elements of this invention, reference is made to *Research Disclosure*, December 1978, Item 17643, published by Industrial Opportunities Ltd, Homewell Havant, Hampshire, P09 1EF, U.K., the disclosures of which are incorporated herein by reference. This publication is identified hereafter by the term "Research Disclosure".

The silver halide emulsions employed in the elements of this invention can be either negative-working or positive-working. Suitable emulsions and their preparation are described in Research Disclosure Sections I and II and the publication cited therein. Suitable vehicles for the emulsion layers and other layers of elements of this invention are described in Research Disclosure Section IX and the publications cited therein.

In addition to the couplers of this invention, the elements of the invention can include additional couplers as described in Research Disclosure Section VII, paragraphs D, E, F and G and the publications cited therein. These couplers can be incorporated in the elements and emulsions as described in Research Disclosure Section VII, paragraph C and the publications cited therein.

The photographic elements of this invention or individual layers thereof, can contain brighteners (see Research Disclosure Section V), antifoggants and stabilizers (see Research Disclosure Section VI), antistain agents and image dye stabilizers (see Research Disclosure Section VII, paragraphs I and J), light absorbing and scattering materials (see Reserach Disclosure Section VII), hardeners (see Research Disclosure Section XI), plasticizers and lubricants (see Research Disclosure Section XII), antistatic agents (see Research Disclosure Section XIII), matting agents (see Research Disclosure Section XVI), and development modifiers (see Research Disclosure Section XXI).

Preferred color developing agents are p-phenylene diamines. Especially preferred are 4-amino-N,N-diethylaniline hydrochloride, 4-amino-3-methyl-N,N-diethylaniline hydrochloride, 4-amino-3-methyl-N-ethyl-N-β-(methanesulfonamido)ethylaniline sulfate hydrate, 4-amino-3-methyl-N-ethyl-N-β-hydroxyethylaniline sulfate, 4-amino-3-β-(methanesulfonamido)ethyl-N,N-diethylaniline hydrochloride and 4-amino-N-ethyl-N(2-methoxyethyl)-m-toluidine di-p-toluene sulfonic acid.

With negative-working silver halide this processing step leads to a negative image. To obtain a positive (or reversal) image, this step can be preceded by development with a non-chromogenic developing agent to develop exposed silver halide, but not form dye, then uniformly fogging the element to render unexposed silver halide developable, followed by development in with a chromogenic developer. Alternatively, a direct-positive emulsion can be employed to obtain a positive image.

Development is followed by the conventional steps of bleaching, fixing, or bleach-fixing, to remove silver and silver halide, washing and drying.

The novel couplers of the invention can be incorporated in a sensitive silver halide photographic material by any convenient method, the method chosen depending on the solubility and diffusion resistance of the coupler concerned. References to publications describing methods of coupler incorporation are given in Section XIV of the *Research Disclosure*. Dispersion with the aid of an anionic surfactant of a mixture of the coupler and an involatile organic compound, the latter usually termed as "oil-former" or "coupler solvent", is a well known method which is appropriate in many instances. Those of the new couplers which are dispersible in dilute aqueous alkali can be used in color developing solutions containing p-phenylenediamine color developing agents.

The novel dyes obtained by reaction between the couplers of this invention and the oxidation products of the usual p-phenylenediamine color developing agents—as described in, for example, *Photographic Processing Chemistry*, L. F. A. Mason, Focal Press, London, 2nd Edition (1975) pp 229–235, and *Modern Photographic Processing*, Grant Haist, Wiley, New York (1979), Volume 2, pp 463–8—have better stability to light than those obtained from the previously known pyrazolotriazole couplers with a methyl group at the 6-position. Nevertheless further enhancement of their light stability is advantageous. Of the many types of compounds which have been proposed as photographic image dye stabilizers, the alkoxybenzene dye image stabilizer, such as 1,2,4,5-tetraalkoxybenzenes in which the alkyl portion of each alkoxy group has 1 to 20 carbon atoms, are particularly effective. Branched chain alkyl groups are possible in the alkoxy groups. These dye image stabilizers are included among the benzene derivatives described in U.K. patent application No. 2,004,078A. The chosen stabilizer compound is conveniently incorporated in a sensitive photographic material by mixing with the coupler before the preparation of the coupler dispersion. A molar quantity of the stabilizer of from 0.2 to 2.0 times the molar quantity of the coupler is usually appropriate.

Formation of a dye according to the invention is carried out by reacting a coupler as described with the oxidized form (DOX) of a color developing agent, such as a p-phenylenediamine color developing agent. Examples of useful p-phenylenediamine color developing agents are represented by the general formula:

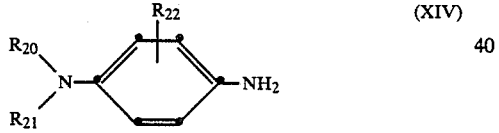

(XIV)

wherein each of $R_{20}$ and $R_{21}$ is an alkyl or substituted alkyl group, $R_{22}$ is hydrogen or one or more simple substituents such as alkyl, alkoxy or alkyl substituted with such groups as carboxyl, sulfonic acid, alkanesulfonamido and hydroxy. They are commonly available in the form of salts such as the hydrochlorides or sulfates. A dye according to the invention is, for example, represented by the formula:

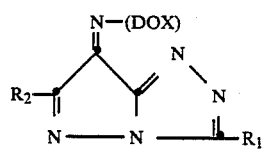

wherein $R_1$ and $R_2$ are as described and (=N—DOX) is a moiety derived from an oxidized photographic color developing agent. For example, when a coupler of the invention (i.e., a compound of Formula III(a) or III(b)) reacts with the oxidation product of a p-phenylenediamine developing agent of Formula XIV, the dye produced has the formula:

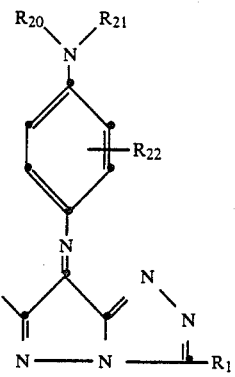

(XV)

wherein $R_1$, $R_2$, $R_{20}$, $R_{21}$ and $R_{22}$ are as described.

Examples of dyes of the invention are given in Table 2. They are designated 1:CD3 and so on, being obtained from the couplers 1 to 7 of Table 1 by reaction with the oxidation product of the well known color developing agent CD-3. The latter has the formula:

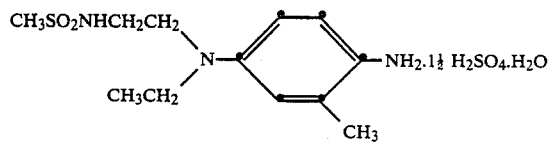

The spectral absorption parameters quoted for each dye in Table II refers to dye generated in coatings of the appropriate couplers as described in Example 1 below.

TABLE 2

| Dye | λmax (μm) |
|---|---|
| 1: CD3 | — |
| 2: CD3 | 552 |
| 3: CD3 | 551 |
| 4: CD3 | 545 |
| 5: CD3 | 544 |
| 6: CD3 | 551 |
| 7: CD3 | 546 |

The following examples illustrate the invention.

EXAMPLE 1

(a) Preparation of coupler coatings

Coupler (1.28 mmole) and an equal weight of di-n-butylphthalate were dissolved in ethyl acetate (1 g) and the resulting solution was added to 10% aqueous gelatin (20 g) at 40° C. A small amount of surfactant (di-isopropyl naphthalene sulfonic acid, sodium salt) was added and the mixture dispersed using an ultrasonic probe. Finally the weight was made up to 25 g with water. [In some instances the addition of cyclohexanone (0.5 g) was required to dissolve the coupler.]

Coating melts were prepared by adding to each dispersion 71.8 g of a standard silver chlorobromide photographic emulsion (1.4% Ag, 5.6% Gel). Appropriate quantities of a gelatin hardener (bisvinylsulfonylmethyl ether, BVSME) and a spreading agent were added immediately before coating, giving a total melt volume of 100 ml. Melts were coated on a transparent support at a coverage of 54 ml.m$^{-2}$, and the coatings were allowed to dry under ambient conditions. A protective gelatin supercoat was then applied in the same fashion, giving coatings of the structure below.

The coatings had the following coverages:

| Constituent | Quantity per square meter |
|---|---|
| silver halide | 5000 μmol |
| coupler | 691 μmol = X g |
| coupler solvent | X g |
| gelatin | 3.24 g |
| hardener | 0.026 g |
| gelatin in supercoat | 1.07 g |

(b) Preparation of coatings with added stabilizer

Further coatings were prepared containing stabilizers in addition to the couplers. The preparation of these coatings followed the procedure outlined in Part (a) except that equimolar quantities of coupler and stabilizer were added to the ethyl acetate/n-butylphthalate solutions.

(c) Evaluation of coatings

Test coupler coatings, prepared as described above, were exposed so as to obtain, after photographic development, sample strips having a transmission density of approximately 1.0 at the wavelength of maximum absorption ($\lambda$max). Photographic development was carried out with conventional color developer and bleach-fix solutions, yielding the corresponding CD-3 coupled dye from each coupler. Dye spectral densities were measured using a commercial spectrophotometer.

The sample strips were then exposed to a high intensity fluorescent light source ("Osram"—trademark—"Color Matching" tubes) at a luminous flux level of 13 klux. After suitable times the strips were removed and the absorption spectrum re-measured, as before. The decrease in density at $\lambda$max was used as a measure of the fade of each sample dye.

(d) Comparison of the stability of dyes from corresponding 6-methyl- and 6-t-butyl-pyrazolotriazole couplers Table 3 is a compilation of the measured fades for dyes derived from pairs of pyrazolotriazole couplers, differing only in the substituent in the 6-position of the pyrazolotriazole nucleus. The couplers of the invention Nos. 2-6 are identified in Table 1. The corresponding comparison couplers, having a methyl instead of a t-butyl group at the 6-position, are designated 2C to 6C.

TABLE 3

| Coupler | Initial Density | Fade Time (hr) | Density Change (Fade) |
|---|---|---|---|
| 2C | 1.24 | 300 | −0.41 |
| 2 | 1.14 | 300 | −0.07 |
| 3C | 1.07 | 300 | −0.63 |
| 3 | 1.18 | 300 | −0.21 |
| 4C | 1.06 | 300 | −0.32 |
| 4 | 1.10 | 300 | −0.10 |
| 5C | 1.05 | 240 | −0.55 |
| 5 | 1.13 | 240 | −0.14 |
| 6C | 1.10 | 240 | −0.72 |
| 6 | 1.04 | 240 | −0.08 |

EXAMPLE 2 (comparative example)

(a) Effect of 4-methyl-2,2-dimethyl-7-t-octyl-6-chromanol (S1) on the stability of the dye from Coupler 7

Following the method described in Example 1 coatings were prepared of the Coupler 7 with and without equimolar amounts of the chromanol compound (S1). Light stability measurements were carried out on the image dyes, as described in Part (c) of Example 1. The results (see table below) showed that the stability of the dye was significantly decreased in the presence of the chromanol.

| Coated Dispersion | Initial Density | Fade Time (hr) | Density Change |
|---|---|---|---|
| Coupler 7 | 1.00 | 331 | −0.11 |
| Coupler 7 + S1 | 1.16 | 331 | −0.18 |

(b) Effect of 1,4-dimethoxy-2,5-didecyloxybenzene (S2) on the stability of the dye from Coupler 7

The experiment of Part (a) was repeated using the tetraalkoxybenzene stabilizer (S2) instead of the chromanol S1. In this instance the stability of the dye produced from the coupler was found to be increased by the presence of the addendum, as shown below.

| Coated Dispersion | Initial Density | Fade Time (hr) | Density Change |
|---|---|---|---|
| Coupler 7 | 1.00 | 331 | −0.11 |
| Coupler 7 + S2 | 1.19 | 331 | −0.07 |

EXAMPLE 3

Effect of 1,2,3,4-tetrabutoxy benzene (S3) on the stability of the dye from Coupler 4

The experiment of Example 2(a) was repeated using Coupler 4 instead of Coupler 7, and the title compound (S3) instead of the chromanol addendum. The results (shown below) demonstrated that the presence of S3 reduced the rate of fade of the dye produced from Coupler 4.

| Coated Dispersion | Initial Density | Fade Time (hr) | Density Change Fade |
|---|---|---|---|
| Coupler 4 | 1.13 | 282 | −0.11 |
| Coupler 4 + S3 | 1.15 | 282 | −0.08 |

EXAMPLE 4

Effect of 1,4-dimethoxy-2,5-bis(2-ethylhexyloxy)benzene (S4) on the stability of the dye from Coupler 4

The experiment of Example 3 was repeated using the title compound (S4) instead of 1,2,3,4-tetrabutoxybenzene (S3). As in Examples 2(b) and 3, stabilization of the dye was observed in the presence of the addendum. The results are shown below.

| Coated Dispersion | Initial Density | Fade Time (hr) | Density Change Fade |
| --- | --- | --- | --- |
| Coupler 4 | 1.00 | 450 | −0.25 |
| Coupler 4 + S4 | 1.02 | 450 | −0.10 |

EXAMPLE 5

Preparation of Coupler 1

In the following description, the roman numerals refer to the general formulae given hereinabove.

(a) t-Butyl N'-(3-t-butyl-4-cyanopyrazol-5-yl)carbazate (VII, $R_2$=t-Bu)

A mixture of the bis-methylthio compound (IV, $R_2$=t-Bu) (13.74 g, 60 mmole), t-butyl carbazate (7.92 g, 60 mmole) and methanol (600 ml) was stirred at room temperature for 5 hours, after which methanol (60 ml) and hydrazine hydrate (6 ml, 120 mmole) were added and the mixture heated under reflux for 2 hours. The solvent was removed and the syrup partitioned between ether (300 ml) and water (60 ml). The organic extract was washed with water (60 ml) dried and the solvent removed to give an oil which was recrystallized from chroroform to give the product as a 1:1 product:-chloroform adduct 16.3 g (68%) m.p., 151°–53° C. (softening 132° C.).

Found: C, 42.1; H, 5.4; N, 17.6. $C_{14}H_{22}Cl_3N_5O_2$ requires: C, 42.2; H, 5.5; N, 17.6.

(b) 3-t-Butyl-4-cyanopyrazole-5-yl hydrazinium hydrochloride (VIII, $R_2$=t-Bu)

The compound from (a) (VIII, $R_2$=t-Bu, $CHCl_3$ adduct) (3.5 g, 8.8 mmole), methanol (12 ml) and 10-M HCl (1.5 ml, 15 mmole) were heated under reflux for 30 minutes. The solvent was removed, THF added and the solvent again removed. The residue was triturated with ether (50 ml) to give a solid which was collected and dried to give the product 1.9 g (100%) m.p. 245°–246° C. (dec.).

Found: C, 44.0; H, 6.4; Cl, 16.8; N, 32.0. $C_8H_{14}ClN_5$ requires: C, 44.5; H, 6.5; Cl 16.5; N, 32.5%.

(c) 3-t-Butyl-4-cyano-5-[2,4,6-trimethyl-3-nitrobenzylidene)-hydrazino]pyrazole (X, $R_2$=t-Bu, Ar=2,4,6-trimethyl-3-nitrophenyl)

The pyrazole from (b) (VIII, $R_2$=t-Bu) (69.9 g, 0.325 mmole), 2,4,6-trimethyl-3-nitrobenzaldehyde (63.1 g, 0.325 mmole), and triethylamine (32.5 g) were heated in refluxing ethanol (325 ml) for 2 hours. The solution was cooled and water (650 ml) added slowly with stirring. The resulting solid was collected, washed with 20% ethanol (650 ml) and then triturated with ether (1250 ml) to give the product 81.8 g (71%) as a white solid m.p. 221°–222° C.

Found: C, 60.8; H, 6.2; N, 23.5. $C_{18}H_{22}N_6O_2$ requires: C, 61.0; H, 6.2; N, 23.7%.

(d) 6-t-Butyl-7-cyano-3-(2,4,6-trimethyl-3-nitrophenyl)-1H-pyrazolo-[3,2-c]-s-triazole (XI, $R_2$=t-Bu, Ar=2,4,6-trimethyl-3-nitrophenyl).

Bromine (28.0 g, 0.175 mmole), in acetic acid (240 ml) was added dropwise to a stirred solution of the hydrazone from (c) (40.3 g, 0.114 mole) in acetic acid (390 ml) and sodium acetate (38 gm, 0.464 mole) at room temperature. After addition was complete, the reaction mixture was heated on a steam bath at 84°–86° C. for 1 hour. Acetic acid (375 ml) was removed under reduced pressure and the reaction mixture poured into water to give a solid which was collected, washed well with water, and dried at 50° for 48 hours to give the product 35.3 g (88%) m.p. 265°–266° C.

Found: C, 60.9; H, 5.7; N, 23.8. $C_{18}H_{20}N_6O_2$ requires: C, 61.2; H, 5.9; N, 23.8%.

(e) 6-t-Butyl-3-(2,4,6-trimethyl-3-nitrophenyl)-1H-pyrazolo-[3,2-c]-s-triazole (III(a), $R_2$=t-Bu, $R_3$=H, $R_1$=2,4,6-trimethyl-3-nitrophenyl): Coupler 1

The nitrile from (d) (30 g, 85 mole) in 75% sulfuric acid (480 ml) was heated and stirred at 120°–124° C. for 25 minutes and then at 140° for 95 minutes. The cooled solution was added dropwise to ice (1200 g) and the mixture adjusted to pH 7 by addition of 50% sodium hydroxide. The solid was collected, washed thoroughly with water, and dried at 50° for 24 hours to give the product as the hydrate 22.2 g (76%) m.p. 249°–250° C.

Found: C, 59.3; H, 6.2; N, 20.5. $C_{17}H_{21}N_5O_2O$ requires: C, 59.1; H, 6.6; N, 20.3%.

EXAMPLE 6

Preparation of Coupler 2

(a) 1-Acetyl-6-t-butyl-3-(2,4,6-trimethyl-3-nitrophenyl)-1H-pyrazolo[3,2-c]-s-triazole Acetyl chloride (12 g, 154 mmole) in THF (80 ml) was added dropwise to a stirred solution of Coupler 1 (22.5 g, 65.2 mmole) in pyridine (110 ml) keeping the temperature below 15° C. The reaction mixture was stirred for a further 2 hours and then added slowly to ice cold water (2000 ml) and methanol (200 ml). After 30 minutes the solid was collected, washed with water, and dried to give the product 24.1 g (100%) m.p. 169°–171° C.

Found: C, 61.0; H, 6.4; N, 18.2. $C_{19}H_{23}N_5O_3$ requires: C, 61.6; H, 6.5; N, 18.9%.

(b) 1-Acetyl-6-t-butyl-3-(3-amino-2,4,6-trimethylphenyl)-1H-pyrazolo[3,2-c]-s-triazole Acetic acid (0.5 ml) was added to Raney nickel (8 spoon-spatulas full) and after washing with THF the catalyst was added to the product of part (a) (16.6 g, 44.9 mmole) in THF (160 ml). The resulting mixture was shaken in an atmosphere of hydrogen at atmospheric pressure for 4 hours and then filtered, the catalyst washed with THF and the filtrate evaporated to give a solid (14.1 g). This material was chromatographed on a dry deactivated silica gel column eluting with 1% ethyl acetate in methylene chloride to give the partially hydrated product, m.p. 206°–207° C., 12.7 g (83%).

Found: C, 66.4; H, 7.5; N, 19.9. $C_{19}H_{25}N_5O$. $0.25H_2O$ requires: C, 66.4; H, 7.4; N, 20.0%.

(c) N-(3-[6-t-Butyl-1H-pyrazolo[3,2-c]-s-triazol-3-yl]-2,4,6-trimethylphenyl)-2-(4-n-butanesulfonamidophenoxy)n-tetradecanamide: Coupler 2

2-(4-n-Butylsulfonamidophenoxy)-n-dodecanoyl chloride (16.6 g, 35 mmole) in THF (35 ml) was added to a suspension of the product of part (b) (11.9 g, 35 mmole) and sodium bicarbonate (4.2 g) in THF (95 ml). After 22 hours, more THF (45 ml) and potassium hydroxide (7.9 g; 140 mmole) in water (175 ml) were added and stirring continued for a further 80 minutes. 3M HCl (100 ml) was added and the THF removed by evaporation under reduced pressure. Dichloromethane (250 ml) was added and the organic extract separated, washed with saturated NaCl, (2×150 ml) dried and evaporated to give the product 23.7 g (92%) m.p. 117°–120° C.

Found: C, 64.7; H, 8.3; N, 10.9; S, 4.4; $C_{41}H_{62}N_6O_4S$. $1\frac{1}{2}H_2O$ requires: C, 64.7; H, 8.5; N, 11.0; S, 4.2%.

EXAMPLE 7

Preparation of Coupler 3

(a)

1-Acetyl-6-t-butyl-7-chloro-3-(2,4,6-trimethyl-3-nitrophenyl)-1H-pyrazolo-[3,2-c]-s-triazole Sulfuryl chloride (8.76 g, 64.9 mmole) in acetic acid (30 ml) was added to a solution of the product of part (a) of Example 6 (24 g, 69.9 mmole) in acetic acid (300 ml) at room temperature with stirring. After 10 minutes the solution was poured slowly into water (900 ml) and the solid collected, washed with water (750 ml) and dried at 50° C. for 16 hours to give the product 24.7 g (94%) m.p. 188°–191° C.

Found: C, 56.4; H, 5.4; N, 17.5 Cl, 8.5.$C_{19}H_{22}ClN_5O$ requires: C, 56.5; H, 5.2; N, 17.3; Cl, 8.8%.

(b)

1-Acetyl-6-t-butyl-7-chloro-(3-amino-2,4,6-trimethylphenyl)-1H-pyrazolo-[3,2-c]-s-triazole (6f)

The product of part (a) of this Example (24.3 g, 60.1 mmole) was reduced under the conditions described in part (b) of Example 6 to give after chromatography the partially hydrated product in p. 211°–213° C., 15.5 g (77%).

Found: C, 60.3; H, 6.3; N, 1.5 Cl, 9.9$C_{19}H_{24}ClN_5O$ requires: C, 60.3; H, 6.5; N, 18.5; Cl, 9.4%.

(c) Coupler 3

This material (72%) m.p. 132°–134° was prepared from the product of part (b) using the method described for Coupler 2 (see Example 6, part (c)).

Found: C, 61.8; H, 7.7; N, 10.2; Cl, 6.2; S, 4.2.$C_{41}H_{61}C_1N_6O_4S$. $1\frac{1}{2}H_2O$ requires: C, 61.8; H, 8.0; N, 10.6; Cl, 4.5; S, 4.0%.

EXAMPLE 8

Preparation of Coupler 4

(a)

3-t-Butyl-4-cyano-5-[4-n-decyl-2,3,5,6-tetramethylbenzylidene)-hydrazino]pyrazole Triethylamine (30 ml, 210 mmole) was added to a mixture of 3-t-butyl-4-cyanopyrazole-5-hydrazinium chloride (45 g, 210 mmole) and 4-n-decyl-2,3,5,6-tetramethylbenzaldehyde in ethanol (400 ml). The mixture was heated under reflux for 4 hours, cooled and dripped into water (2000 ml). The solid was collected, washed and dried to give the product (90–100%) which was of sufficient purity for use in the next stage.

(b)

6-t-Butyl-7-cyano-3-(4-n-decyl-2,3,5,6-tetramethylphenyl)-1H-pyrazolo[3,2-c]-s-triazole Bromine (28 g, 175 mmole) in acetic acid (100 ml) was added dropwise with stirring to a suspension of the hydrazone from part (a) (175 mmole) and sodium acetate (57.4 g, 700 mmole) in acetic acid (450 ml) at 40°–50°. When addition was complete (10 minutes) the mixture was heated at 80°–90° for 1 hour, cooled and dripped into water (3.5l). The solid was collected, washed well, dried and crystallized from n-decane to give the product (70–90%) m.p. 190°–192° C.

Found: C, 74.1; H, 9.2; N, 14.9 $C_{29}H_{43}N_5$ requires: C, 75.5; H, 9.3; N, 15.2%.

(c)

6-t-Butyl-3-(4-n-decyl-2,3,5,6-tetramethylphenyl)-1H-pyrazolo-[3,2-c]-s-triazole: Coupler 4

The nitrile from part (b) (20 g) was added in one portion to 75% sulfuric acid (from concentrated $H_2SO_4$[270 g]) and ice (90 g) with stirring at 140°–150° C. 15–20 minutes later, ice (1000 g) was added. After decantation, the sticky solid was dissolved in methanol (200 ml) and hot water (5 ml) added. On cooling, the precipitate was collected, washed with 90% methanol (2×50 ml) and dried to give the product (85–90%), m.p. 194°–195° C.

Found: C, 76.9; H, 10.4; N, 12.8% $C_{28}H_{44}N_4$ requires: C, 77.1; H, 10.1; N, 12.8%.

The invention has been described in detail with particular reference to preferred embodiments thereof, but it will be understood that variations and modifications can be effected within the spirit and scope of the invention.

What is claimed is:

1. In a photographic element comprising a support bearing at least one silver halide emulsion layer having associated therewith a pyrazolo[3,2-c]-s-triazole dye-forming coupler the improvement wherein said coupler contains in the 6-position a substituted or unsubstituted tertiary alkyl group and in the 3-position a phenyl group containing alkyl groups in the 2-, 4- and 6-positions of the phenyl group.

2. A photographic element comprising a support bearing at least-one silver halide emulsion layer having associated therewith a dye-forming coupler represented by the formula:

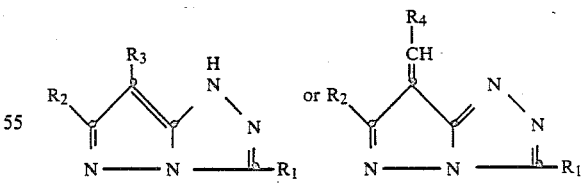

wherein $R_1$ is phenyl containing alkyl groups in the 2-, 4- and 6-positions of the phenyl group;

$R_2$ is unsubstituted tertiary alkyl or substituted tertiary alkyl;

$R_3$ is hydrogen or coupling-off group and $CHR_4$ is a coupling-off group.

3. A photographic element as in claim 2 wherein $R_1$ is a phenyl group containing methyl groups in the 2-, 4- and 6-positions of the phenyl group.

4. A photographic element as in claim 2 wherein $R_2$ is t-butyl and $R_1$ is one of the following:

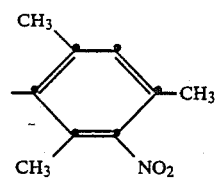

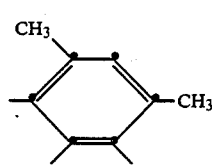

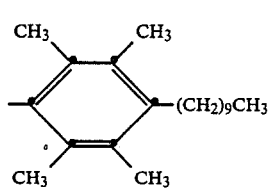

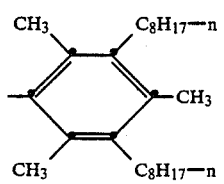

wherein Z is a ballast group.

5. A photographic element as in claim 1 comprising an alkoxybenzene dye image stabilizer.

6. A photographic element as in claim 1 comprising a 1,2,4,5-tetraalkoxybenzene dye image stabilizer in which each alkoxy group contains 1 to 20 carbon atoms.

7. A photographic element as in claim 1 comprising 1,2,3,4-tetrabutoxy benzene.

8. A process of developing an image in a photographic element comprising a support and a silver halide emulsion containing an imagewise distribution of developable silver halide grains, the process comprising the step of developing the element with a silver halide color developing agent in the presence of a dye-forming pyrazolo[3,2-c]-s-triazole dye-forming coupler having in the 6-position of the coupler a substituted or unsubstituted tertiary alkyl group and in the 3-position a phenyl group containing alkyl groups in the 2-, 4- and 6-positions of the phenyl group.

9. A process of developing an image in a photographic element comprising a support and a silver halide emulsion containing an imagewise distribution of developable silver halide grains, the process comprising the step of developing the element with a silver halide color developing agent in the presence of a dye-forming coupler represented by the formula:

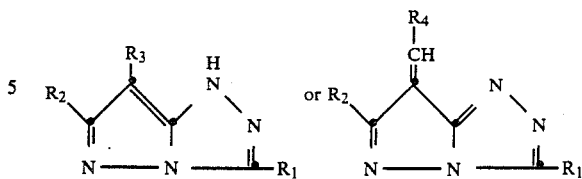

wherein $R_1$ is phenyl containing alkyl groups in the 2-, 4- and 6-positions of the phenyl groups;

$R_2$ is unsubstituted tertiary alkyl or substituted tertiary alkyl;

$R_3$ is hydrogen or coupling-off group and $CHR_4$ is a coupling-off group.

10. A process as in claim 9 wherein $R_1$ is a phenyl group containing methyl groups in the 2-, 4- and 6-positions of the phenyl group.

11. A process as in claim 9 wherein $R_2$ is t-butyl and $R_1$ is one of the following:

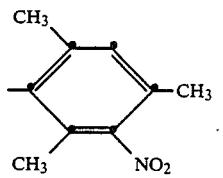

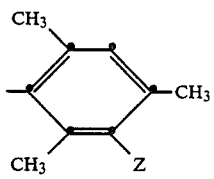

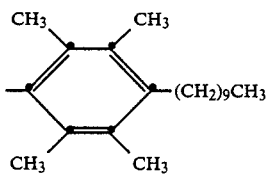

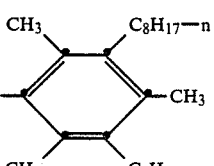

wherein Z is a ballast group.

12. A process as in claim 9 wherein said photographic element comprises an alkoxybenzene dye image stabilizer.

13. A process as in claim 9 wherein said photographic element comprises a 1,2,4,5-tetraalkoxybenzene dye image stabilizer in which each alkoxy group contains 1 to 20 carbon atoms.

14. A process as in claim 9 wherein said silver halide color developing agent is a paraphenylenediamine color developing agent.

* * * * *